United States Patent
Douglas et al.

(10) Patent No.: US 6,750,962 B2
(45) Date of Patent: Jun. 15, 2004

(54) OPTICS ALIGNMENT AND CALIBRATION SYSTEM

(75) Inventors: Joel S. Douglas, Los Altos Hills, CA (US); Jeffrey N. Roe, San Ramon, CA (US); John H. Priest, Everett, WA (US); John M. Gleisner, Lynnwood, WA (US); Charles C. Raney, Scotts Valley, CA (US); David A. Hasker, San Jose, CA (US); Ryszard Radwanski, Morgan Hill, CA (US); John Ramirez, Sunnyvale, CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

(21) Appl. No.: 09/828,874

(22) Filed: Apr. 10, 2001

(65) Prior Publication Data

US 2002/0067484 A1 Jun. 6, 2002

Related U.S. Application Data

(63) Continuation of application No. 09/206,641, filed on Dec. 7, 1998, now Pat. No. 6,285,454.

(51) Int. Cl.[7] .............................................. G01N 1/10
(52) U.S. Cl. ...................................... 356/246; 356/440
(58) Field of Search ............................. 356/446, 246; 422/82.05, 82.09; 436/169; 600/300, 322

(56) References Cited

U.S. PATENT DOCUMENTS

| | | | |
|---|---|---|---|
| 4,637,403 A | 1/1987 | Garcia et al. | |
| 4,833,088 A | * 5/1989 | DeSomine et al. | ......... 435/289 |
| 4,994,167 A | 2/1991 | Shults et al. | |
| 5,053,199 A | 10/1991 | Keiser et al. | |
| 5,232,668 A | 8/1993 | Grant et al. | ............. 422/82.05 |
| 5,279,294 A | 1/1994 | Anderson et al. | |
| 5,304,468 A | 4/1994 | Phillips et al. | |
| 5,410,474 A | 4/1995 | Fox | ........................ 364/413.07 |
| 5,515,170 A | 5/1996 | Matzinger et al. | |
| 5,522,255 A | 6/1996 | Neel et al. | |
| 5,580,794 A | 12/1996 | Allen | |
| 5,795,543 A | * 8/1998 | Poto et al. | ..................... 422/55 |
| 5,989,917 A | * 11/1999 | McAleer et al. | .............. 436/46 |
| 6,009,632 A | 1/2000 | Douglas | |
| 6,285,454 B1 | * 9/2001 | Douglas et al. | ............. 356/446 |

FOREIGN PATENT DOCUMENTS

| | | | |
|---|---|---|---|
| DE | 692 22 523 T2 | 5/1998 | |
| EP | 0 351 891 B1 | 1/1990 | |
| EP | 0 353 589 | 2/1990 | .......... G01N/33/53 |
| EP | 0 383 209 A1 | 8/1990 | |
| EP | 573598 | * 9/1992 | |
| WO | WO 92/15861 | 9/1992 | |
| WO | WO 96/13707 | 5/1996 | |
| WO | WO 98/19159 | 5/1998 | .......... G01N/33/52 |

* cited by examiner

*Primary Examiner*—Zandra V. Smith
(74) *Attorney, Agent, or Firm*—Woodard Emhardt Moriarty McNett & Henry LLP

(57) ABSTRACT

A multi-use assay system accurately docks a removable test strip supporting a reagent-analyte reaction with an optics system including an LED, photodetector, and lenses or light pipes for directing light to and from the test strip. Docking is achieved using alignment fixturing, whereby an optics block holder is relied upon to align the test strip and test pad with the various optical components. Signals from the photodetector indicative of test strip reaction progress are provided to a processor for measuring the analyte.

4 Claims, 4 Drawing Sheets

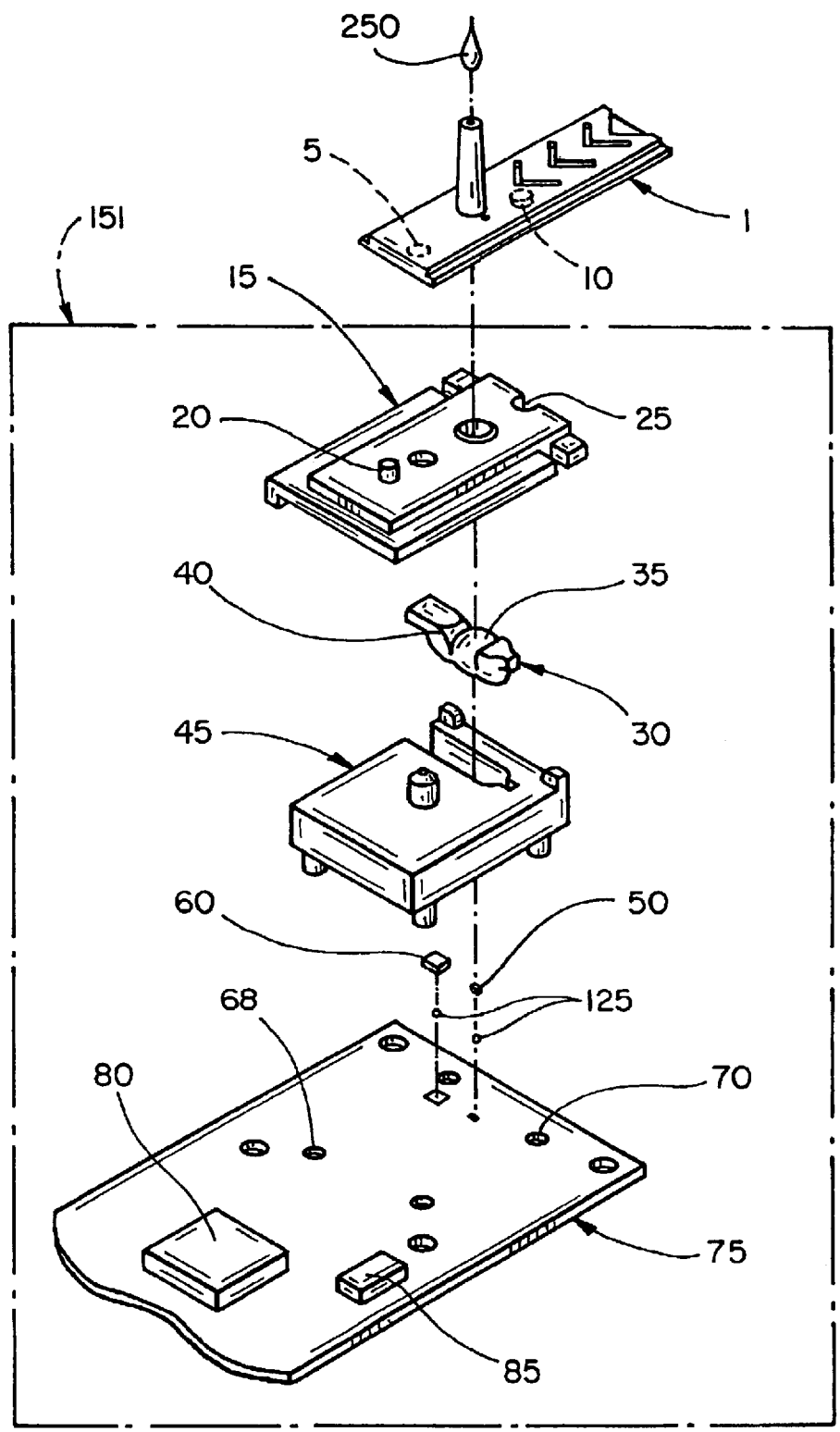
FIG_1

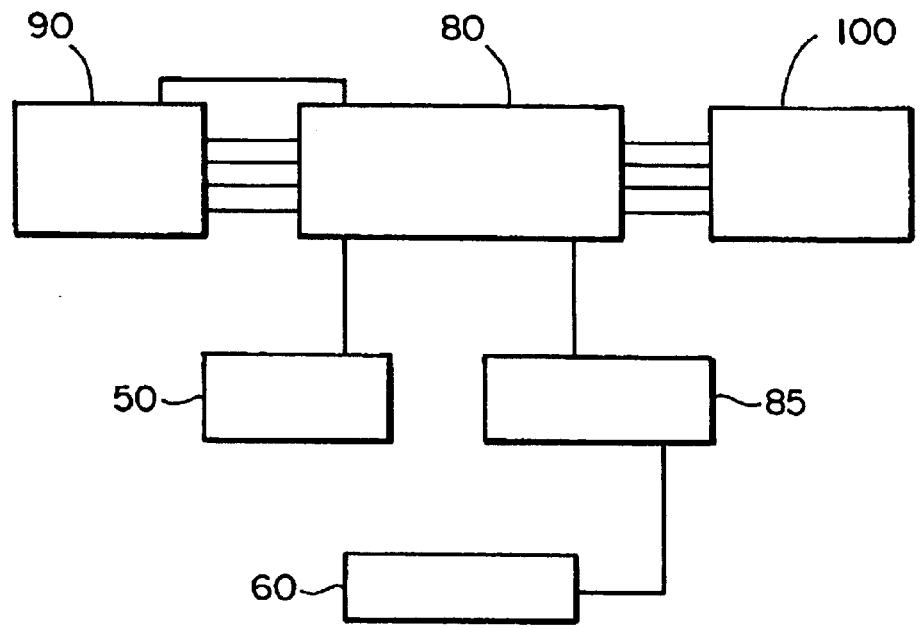
FIG_2
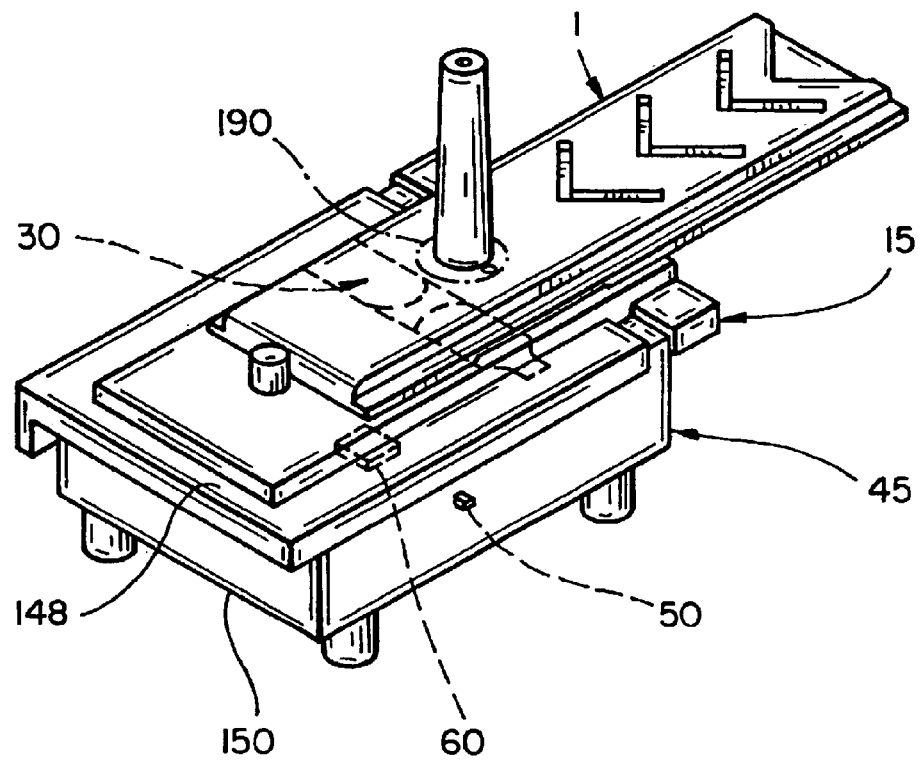
FIG_4

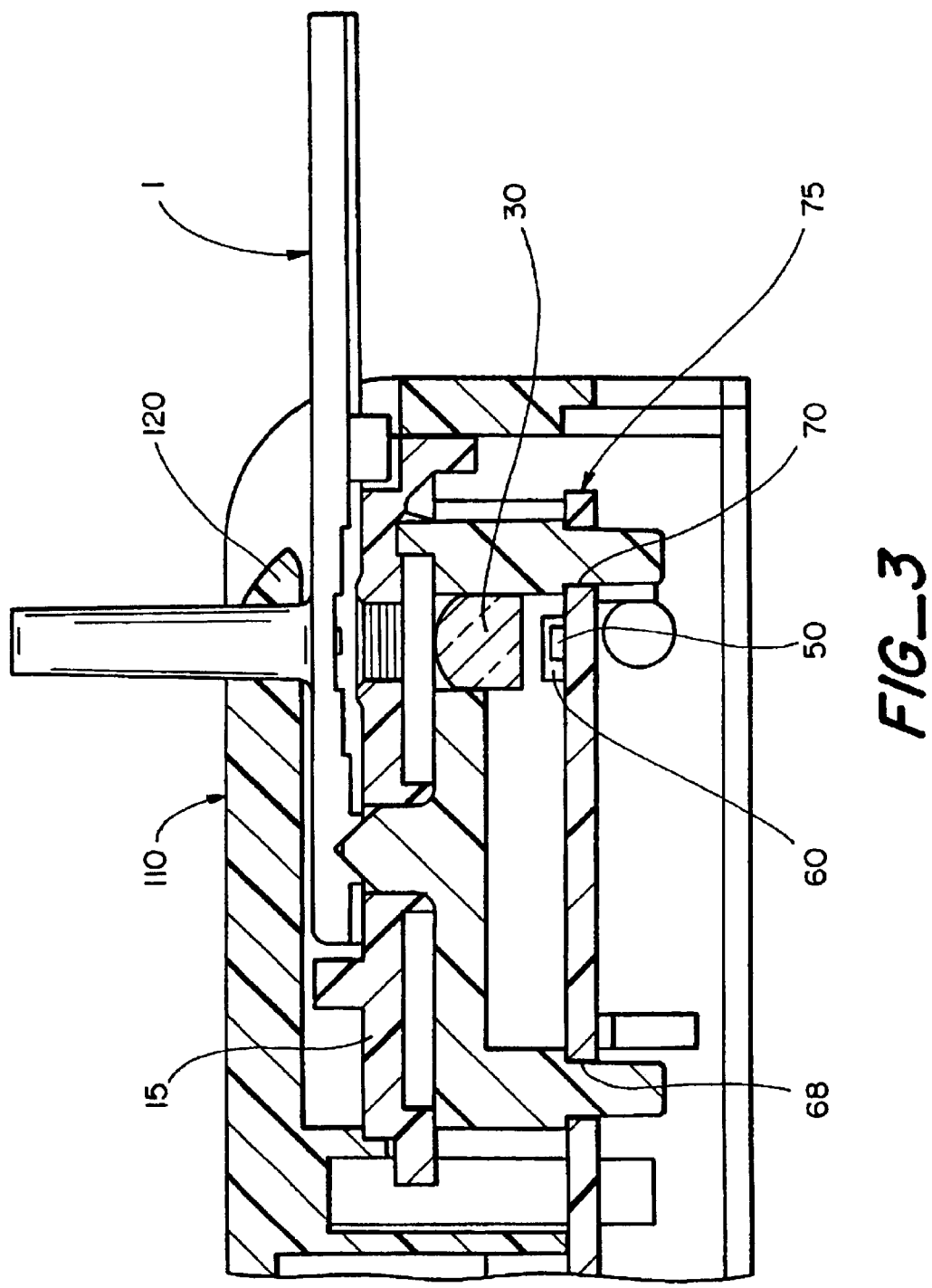
FIG_3

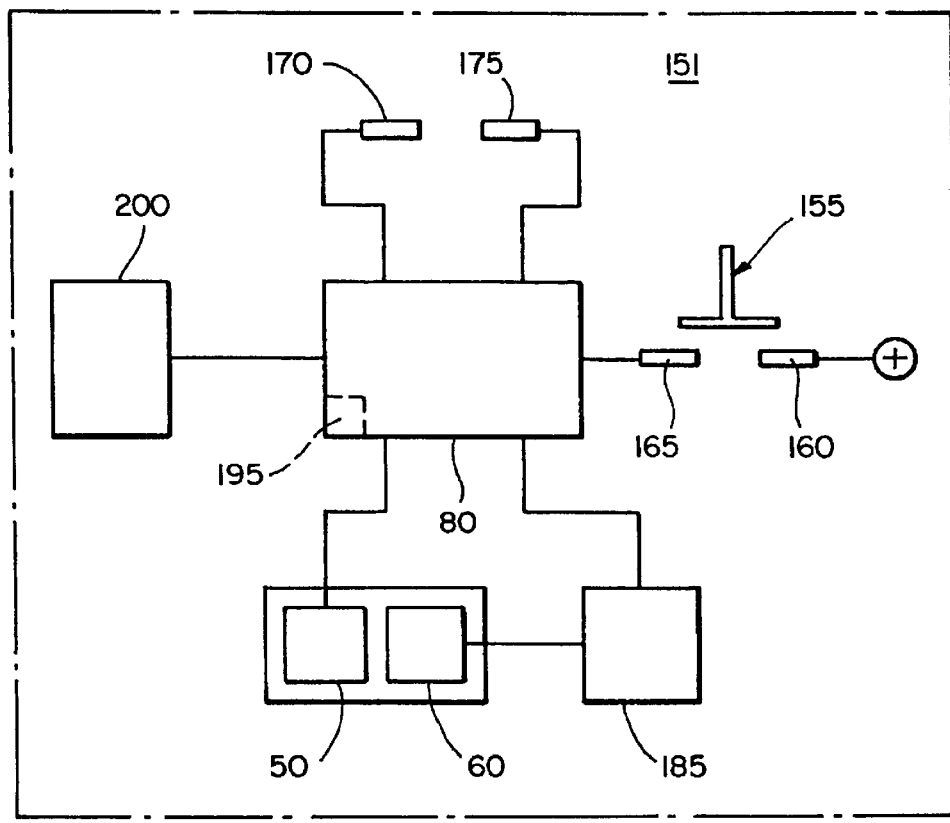
FIG_5A
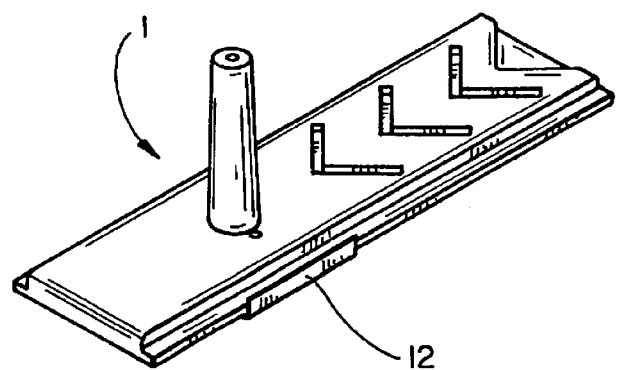
FIG_5B

OPTICS ALIGNMENT AND CALIBRATION SYSTEM

This application is a continuation of application Ser. No 09/206,641, filed on Dec. 7, 1998 now U.S. Pat. No. 6,285,454.

FIELD OF THE INVENTION

The present invention relates to a method and device for the determination of an analyte in a body fluid sample and providing a means of reliably incorporating calibration information when each test is conducted.

BACKGROUND OF THE INVENTION

Many qualitative and quantitative diagnostic self-tests have developed in the clinical field utilizing bodily fluids from humans or animals as a sample. Many such devices have been developed for the analysis of blood glucose in humans. However, additional analytes may be found and the concentration determined if the appropriate low cost system was available.

One common means for the determination of an analyte in a body fluid sample is through the use of reflectance measurements using a spectrophotometer and test strip or by alternatively using a biosensor system. The biosensor system has been popular in more recent times because of the ability for a biosensor to use small sample sizes 3 to 5 $\mu$ls where as traditional reflectance systems usually require substantially more sample in the range of 5 to 10 $\mu$ls. However, the biosensor systems tend to be affected by numerous interference's found in the body fluid samples whereas, the reflectance measurements tend to be less affected and therefor provide more accurate results The need for a low cost system which permits low volume sample size utilization and accurate results is important to the diagnostic field and could make the monitoring of chronic disease applications more achievable.

The National Institute of health conducted a large scale study to evaluate the benefit of long term tight control of blood glucose monitoring. The study known as the DCCT proved that long term tight control of the blood glucose levels in patients with diabetes had a direct relationship to the health of the patient. One way for the medical profession to monitor the control of their patients is through the use of low cost, convenient monitors with memory.

Many diabetics currently use a test method described in U.S. Pat. No. 5,304,468 to Phillips et al. This system is comprised of an electronic meter and disposable dry reagent test strip. The meter reads the color change of the test strip after the blood sample has been applied and converts this to an approximate reading of the concentration of glucose in the blood sample. The test strips have some variation to them and the patient must select the appropriate calibration level prior to using the test strip to monitor their blood. In this way the meter can accommodate various strip performance issues. The system also uses a complex dual optics system to resolve the reflectance reading.

U.S. Pat. No. 4,637,403 to Garcia et al. Describes an integrated system which provides a method by which the patient lances the finger to get a sample of blood which is then used by the device to provide a reading of the blood glucose or other analyte concentration. This system uses a complex reflectance system to read the analyte level in the sample.

U.S. Pat. No. 5,279,294 to Anderson et al. describes a hand held shirt pocket device for the quantitative measurement of glucose in a blood sample. The device uses sophisticated optics and test strip system to achieve a reading.

U.S. Pat. No. 5,515,170 to Matzinger et al. Describes at the difficulties of keeping a reagent test strip aligned with an optics system.

European Patent Specification 0 351 891 B1 Hill et al. Describes an electrochemical sensor system and electrodes which are suitable for measuring the concentration of an analyte in a body fluid sample. The system requires the use of expensive electrodes and reader to determine the analyte concentration level.

U.S. Pat. No. 4,994,167 to Shults et al. describes a measuring device for determining the presence and amount of a substance in a biological fluid using electrochemical means.

U.S. Pat. No. 5,580,794 to Allen et al. describes a single use disposable-measuring device for determining the presence and amount of a substance in a biological sample using reflectance methods. The system uses optics and electronics which are mated on a single plane.

U.S. Pat. No. 5,522,255 to Neel et al. Describes a fluid dose, flow and coagulation device which uses a non-volatile electronic calibration device to check the calibration of the reagent strip.

U.S. Pat. No. 5,053,199 to Keiser et al. describes a biosensing meter with a pluggable memory key. This device uses a plugable memory key to control the operations of the meter.

The above patent disclosures are incorporated herein by reference in their entirety.

Although many improvements have been made, the cost and complexity needed to read the analyte concentration of a body fluid is still significant. The need to match calibration of a meter to the strips and the system of holding a test strip in alignment with the optics has been problematic and led to numerous errors in analyte concentration readings.

Currently, existing calibration mechanisms require the loading of a calibration chip, strip or manually inputting a calibration code into the meter. These devices can be reused numerous times resulting in errors by the patient who do not change or enter the appropriate calibration data.

In addition, a system which requires a smaller body fluid sample would make it more convenient for the patient and coupled with the improved accuracy found in reflectance devices compared to electro chemical would make the monitoring simpler and more accurate.

An additional issue is the use of test strips which are out of date. Old test strips which are expired can lead to errors and inaccurate results. By providing a means to eliminate the use of expired test strips the patients will not have to monitor the expiration date of the test strips and eliminates patient errors from using old test strips.

SUMMARY OF THE INVENTION

The invention overcomes the deficiencies found in current devices described in the prior art by providing a system which is specifically designed to focus the optical signal from the emitting source and back to the detecting device after being reflected off of a test strip which changes color based on a scalable chemical reaction. The instrument can use either focused lenses or light piping to direct the light from the emitter to the test strip reflectance surface and focus the reflected light back to the detection system. By doing this, the system permits the use of small amounts of test strip carrier to be used which reduce the amount of sample absorbed in the test strip carrier. The key to accomplishing this is to provide the means to focus the light on a small site and refocus the reflected light so that it is channeled to the appropriate detector. The means of focusing also permits the use of low cost optical components such as LED's and photodetectors formed from raw die elements and are placed by automated placement equipment with respect to predetermined targets on the printed circuit board.

The system must also be able to accurately dock the test strip with the optics system including led, detector, lenses or light pipes. To achieve this a centerline alignment, or fixturing, system which minimizes rotation of the test strip carrier is required. The need to accurately describe the test strip performance with respect to the analyte concentration also helps accuracy.

An advantageous feature of this system is the use of small sample sizes to test for analyte concentrations. This provides a convenience to the patient not found in the prior art as to the amount of sample required for these devices is in excess of 5 μls.

Another advantage is the minimization of strip to meter calibration errors by using a read writeable calibration system which prevents reuse after the test strip supply is used up, prevents inadvertent use of test strips which are older than the expiration date of the package.

Another advantage is the alignment of the test strip with the meter testing system to provide a means of reducing the error which is need to compensate for poor strip to optics alignment.

This invention provides a multi-use digital electronic instrument that is entirely self-contained. The device consist of a low cost optics system and the optics/lightpiping to provide adequate concentration of emitted and reflected light to perform a reflectance test. The system of this invention is useful in connection with the synchronized test kit and system disclosed in application Ser. No. 08/960,866 filed Oct. 30, 1997, the optics system disclosed in application Ser. No. 08/990,084 filed Dec. 12, 1997, and/or the test system disclosed in application Ser. No. 09/104,749 filed Jun. 25, 1998. The disclosures of the above patent applications are incorporated herein by reference in their entirety.

BRIEF DESCRIPTION OF THE DRAWINGS

Many advantages of the current invention will be apparent to one skilled in the art with a reading of this specification in conjunction with the attached drawings, wherein like references numerals are applied to like elements and wherein:

FIG. 1 is an exploded view of the optics system

FIG. 2 is a schematic of the electronics system showing the calibration device and its relationship to the measurement means.

FIG. 3 is a partial section and an elevation view of the optics system.

FIG. 4 shows the strip alignment features for aligning the strip to the strip holder.

FIG. 5A is a block diagram showing the processing operation of the invention.

FIG. 5B illustrates the test strip with a test pad.

DESCRIPTION OF THE INVENTION

The present invention is preferably utilized in multi-use digital electronic instruments and assay devices described in detail in the above-identified patent applications and previously incorporated by reference.

FIG. 1 is an exploded view of the optics system which comprises use of a strip 1, which has a alignment dentent 5 and pin 10, and comprises optics shield 15 with alignment dentent pin 20 and slot 25, optics lens 30 with led focusing lens 35 and reflectance focusing lens 40, optics block holder 45 which positions the optics block relatively to the optics components LED 50 and photodetector 60 which are aligned to the holes 68 and 70 in the printed circuit board 75. The photodetector 60 and LED 50 are affixed to the printed circuit board 75 by using adhesive 125. The LED 50 and photodetector 60 formed from raw die elements and are place by automated placement equipment with respect to predetermined targets on the printed circuit board hole 68.

The printed circuit board is part of a reflectometer 151 which includes a printed wiring assembly having a printed circuit board (PCB) 75, microprocessor 80 and A to D conversion circuits 85.

Test strip 1 is provided with an alignment mechanism which may have features 5 and 10 designed to mate with features 20 and 25 on optics shield 15. These are designed to issue positive alignment of the test strip to the optics. It is contemplated that other configurations meeting the intent of the invention are within the scope of this invention.

FIG. 2 is a schematic of the electronics system which is attached to the printed circuit board 75 of FIG. 1. These components include components LED 50 and photodetector 60 used to illuminate and collect the reflected light from the test strip, microprocessor 80, A to D conversion circuits 85, calibration EEPROM 90 and electrical communication traces connecting the EEPROM to the microprocessor 80, electrical communication traces connecting the microprocessor and forming a serial communication port 100.

The LED 50 and photodetector 60 are attached to the printed circuit board 75 by the use of die attach and wire bonding. The die attach machine aligns the two devices so that they are located within 0.002 inches of true positioning with respect to alignment holes 68 and 70. This accurate positioning provides the alignment necessary to permit the optics block lenses to accurately focus the light emitted from the LED to be directed and focused on the center of the test strip accurately captured in the optics block shield system.

FIG. 3 is a partial section of an elevation view of the optics system. The test strip 1 is designed to be inserted in the collated system. The meter housing 110 has pressure tongue 120 molded into it. It is designed to provide pressure to the strip 1 so that it is sufficiently locked in place and will not move during testing. The locking system shown in FIG. 1 consisting of features 5, 10, 20 and 25 are used to lock the strip 1 to the shield 15. The optics lens 30 with LED focusing lens 35 and reflectance focusing lens 40 provides the light piping system to direct the light to and from the optics components LED 50 and photodetector 60. Optics block holder 45 positions the optics block relative to the optics components LED 50 and photodetector 60 which are aligned to the holes 68 and 70 in the printed circuit board 75. The photodetector 60 and LED 50 are affixed to the printed circuit board 75 by using adhesive. The optics lens system 30 comprising lens 35 and 40 could be replaced with light piping components such as glass fiber or coated reflective hollow tube.

FIG. 4 shows the strip alignment features for aligning the strip to the strip holder. The alignment features found in the strip 1 are detent 5 and pin 10 which mate with to optics shield 15 with alignment detent pin 20 and slot 25. The optics assembly consisting of optics lens 30, optics shield 15 and optics block holder 45 is a generally planar support having at least a top face 148 and a bottom face 150. The bottom face 150 is configured to receive illumination from the LED 50, and the optics lens 30 directs the illumination to one or more test areas 190 on strip 1. The top face 148 of the optics assembly is also configured to transmit the diffusely reflected optical radiation returning from the sampling areas 190 to the detector 60.

A reference detector may also be incorporated into the invention to provide a means of monitoring the power and the LED performance. This arrangement is designed to permit the system to monitor this performance and allow for compensation as the system ages.

In another aspect of this invention, an optical arrangement in accordance with the invention is provided with a molded plastic lens system 30 to focus light to and from the sample on the test pad 12. Such an arrangement provides the capability of focusing the light to and from a small reaction area, which reduces the size of the test pad 12 and reduces the amount of sample 250 required to effect the testing procedure. Advantages thus realized include reduction in size/cost of the matrix employed and quantity of expensive reagents required. This has the additional benefit of minimizing the sample size required to run the test because the void volume of the matrix times the area dictates the volume of sample required to run the test.

The optics of the invention may include appropriate optical filtering to optimize measurement, or electronic filtering and masking techniques may be employed to improve signal-to-noise levels In another aspect the optical configuration of this invention uses multiple LED and photodetector pairs. A first pair is used to achieve the primary analyte determination. A second pair is used to monitor test initiation and to quantify hemoglobin and hematocrit. Subsequent pairs are used to monitor native color effects of lympic and icteric samples. Additional optical pairs are used in association with added chemical components in the strip for specific determination of possible interference factors such as pH, specific gravity, etc. as well as for specific determination of additional analytes such as cholesterol, triglycerides, etc. Such analysis, using different wavelengths where desired, provides significant benefits to overcoming interfering effects from the sample and the environment. By selecting wavelength pairs which are tuned to detect components of the test, it is possible to isolate and quantify the analyte, hematocrit and red blood cell contributions in a testing event. In accordance with the invention, interference from the environment is minimized by separating its effects and monitoring each one independently using multiple optical systems. Through detection and quantification, the individual contribution to the measurement can be subtracted from the analyte measurement. With the ever decreasing cost of computing power, and a unique of constructing multiple optical systems at very low cost, the approach of the invention is readily applicable to home diagnostic use.

The test strip 1 is comprised of a test pad 12 situated in a test pad holder 13. This holder mounts to strip fluid delivery system 14 and parts 5 and 10 provides a means for accurately positioning the test pad 12 with respect to the LED 50, and the detector 60 in addition to providing a means for blocking ambient light from effecting the analysis. The test pad 12 is impregnated with the appropriate chemistry to permit a colormetric analysis of the analyte being tested and may therefore provide a stable absorbent substrate.

The test strip of this invention provides a support for the test pad. The strip positively seats on the testing instrument, assuring proper alignment through center line fixturing. It also seals the optics area from ambient light and blood contamination. Thus, it provides all of the functionality of a test strip and test strip holder of a conventional reflectance system. The test strip provides additional benefits in being removed after each test, facilitating easy access to the optics area for cleaning if required. With this combination part; the overall cost of the system is further reduced. When inserted into the detection device 151, the test strip 1 contacts complete a circuit which turns the device on. The device is turned off upon removal of the test strip. This eliminates a need for a separate on/off circuit or for patient action to turn the testing instrument on or off.

The signal producing system impregnated in the test pad matrix can be formed from different indicator systems such as 3-methyl-2-benzothiazolinone hydrazone (MBTH) and 8-anilino-1-naphthalenessulfonate(ANS), U.S. Pat. No. 5,453,360 Yu, MBTH and 3-dimethylaminobenzoic acid (DMAB), U.S. Pat. No. 5,049,487 Phillips et al., 3-methyl-2-benzothiazolinone~hydrazone sulfonate sodium salt (MBTH-S04) and ANS, MBTH-S04 and N-(3-sulfopropyl) aniiine (HALPS), MBTH-S04 and N-Ethyl-N-(3-sulfopropyl)aniline ALPS, U.S. Pat. No. 4,396,714, Maeda et. al. and U.S. Pat. No. 5,776,719 Douglas et al. One skilled in the art can select alternate indicator systems. The oxidase enzyme system contained in the reagent pad produces hydrogen peroxide which is used to convert the indicator with the assistance of peroxidase which acts as the catalyst.

In a preferred embodiment the reagents are impregnated into a porous membrane by submerging the dry membrane into a reagent dip. Excess fluid is wiped from the membrane surface and the membrane is gently dried in an oven. At this point, subsequent dipping and drying can be conducted. A preferred embodiment for a two dip process is:
MBTH-S04 & ALPS Formulation

| MBTH-S04 & ALPS Formulation | |
| --- | --- |
| A Dip Final Concentrations In Citrate Buffer, pH 7 | 0.1 M stock |
| A Dip | |
| EDTA | 0.08% |
| mannitol | 0.19% |
| Gantrez-595 | 0.53% |
| Kiucel 99-EF | 20 uM |
| Crotein-SPA | 7.45% |
| enzyme reagents | |
| Glucose Oxidase | 0.92% |
| Peroxidase | 0.54% |
| B Dip | |
| In 70% Ethanol | |
| MBTH-504 | 0.66% |
| ALPS | 2.00% |
| SOS | 0.20% |

The assembly of a system kit comprised of a testing instrument and a specific number of synchronized test strips for the testing of a specific analyte can provide a simple, cost effective test method and procedure.

FIG. 5A is a block diagram showing the processing operation of the invention. Testing instrument 151 comprises a microprocessor 80 which controls the operation of the testing instrument 151. The testing instrument 151 is activated by a switching mechanism which may comprise a mechanical ON button 155 and contacts 160–165 which close an appropriate circuit when the button 155 is depressed. Closing of this circuit triggers operation of the device by notifying the microprocessor 80 that a measurement reading of a positioned test strip 1 is to be performed. The test strip may be one of a number of test strips in the set, and a counter keeps track of these. Alternatively, the circuit may be closed via a fluid connection using the test sample, with the contacts 170 and 175 operating as probes provided for making contact with the test pad 12 of the test strip 1 illustrated in FIG. 5B to thereby activate the testing instrument 151 upon detection of the sample on the appropriately positioned test strip 1.

Following activation, measurement of the reaction of the sample with the reagent on the test strip 1 is effected using the detector 60. The microprocessor 80 derives an electrical signal from the electro-optical devices the LED 50, and the detector 60, and processes it to generate a detection signal indicative of analyte concentration in the tested sample. An ASIC 185 (application-specific integrated circuit) and a memory, such as RAM (random access memory) 195 or a ROM (read only memory) may be used in conjunction with the microprocessor 80, while the results of the measurement may then be displayed using LCD display 200. The results may alternatively be stored in RAM 195 for subsequent viewing or processing. The subsequent processing may be performed using the measuring instrument 151 itself, or using other devices to which the, measurement results can be downloaded. One possibility in accordance with the invention is a modem link with a remote processing unit, using, e.g., telephone lines. The information may also be downloaded for storage at an internet location or electronic bulletin board for subsequent retrieval and processing or review by medical professionals. See application Ser. No. 09/190,301 filed Nov. 13, 1998, incorporated herein by reference in its entirety.

One feature in accordance with the invention is the use of a calibration chip 90 as shown in FIG. 2. The calibration chip is detachably connectable to the testing instrument 151 for electronic communication with the microprocessor 80. It may be any form of volatile or non-volatile memory including single use microprocessors, EPROMs or EEPROMs 90. Calibration chip 90 contains calibration information which is uniquely specific to the reagent provided with a particular set of test strips 1 distributed with the calibration chip. In this way, lot differences in the reagent can be compensated for using the required information and sophistication, while at the same time obviating the need for the user to enter or contribute to this information. This minimizes error and greatly facilitates use and accuracy of the testing instrument of the invention.

The color formed after applying the bodily fluid to the reagent test pad is proportional to the amount of analyte in the applied sample 250. The testing instrument 151, via sensor 60, ASIC 185 and microprocessor 80, measures the change in reflectance due to the development of the specific color generated by the reagent on the test strip 1. This is either used as the input to a function which relates reflectance to analyte level or to a table which correlates reflectance value to analyte level. The function or the table must be stored within the system for it to produce and display, on display 200, a reading of the analyte level in the sample 250. While most meters in use today employ functions to convert reflectance readings to analyte concentration, this approach requires that the function be stable and well understood. The use of a look up table permits the storage of specific values for reflectance and their corresponding analyte levels. The testing instrument uses this table and interpolates between the table values to give relatively accurate readings. This is achievable in a system such as that described by this invention as the table can quickly be generated for each reagent lot produced.

In the preferred embodiment, calibration is based on the response produced by a specific lot of test strips. In this manner, there is no need to presort and test the LED 50, signficancly reducing the cost of the sensor 60. The LED 50 and photodetector 60 formed from raw die elements and are place by automated placement equipment with respect to predetermined targets on the printed circuit board. In addition, this calibration step during manufacture allows the device to compensate for a wide area of variables normally found in reflectance systems. The specific calibration data for the test strips 1 shipped with the testing instrument can be stored in the unit's read only memory (not shown). Alternatively, a master strip can be provided for setting the calibration information for that lot of strips and the master strip can be distributed therewith. A counter may be provided to limit the testing instrument 151 to performing only a specific number of tests which correlates to the quantity of test strips 1 shipped with the device. Other limitations can be built-in, such as expiration date information pertaining to the specific lot of test strips 1, with this information being contained in the measuring intrument's ROM or in the calibration chip 90 or in the master strip.

A more traditional approach to calibration may alternatively be taken. A calibration algorithm, with several settings if necessary, could be programmed into the system if the testing instrument has a longer projected life and is to be used with multiple sets of test strips.

If a microprocessor is used for the calibration chip, the chip may be provided with its own power source for memory information retention. Similarly, when a microprocessor or EEPROM or other memory device is used, the calibration chip 90 may have its data overwritten or an indicator bit thereof be written by the microprocessor 80 following its use to prevent reuse. The calibration information stored in the calibration chip 90 is thus downloaded to the microprocessor 80, and the calibration chip is disabled, preventing re use thereof. The calibration information contains the permitted number of test strip analyses to be performed, the number corresponding to the number of test strips provided with the kit. The calibration chip itself can then be disposed of.

Alternatively, a counter (not shown) may be provided in the calibration chip, the counter being decremented each time the chip is read. In this manner, only a limited number of readings, corresponding to the number of test strips 1 provided with the calibration chip 90, can be performed. It is also contemplated that calibration information provides and expiration date preventing use of the calibration chip and/or associated strips thereafter, or a duration can be measured after which use of the chip and/or associated strips is precluded. The duration can be commenced from time of opening a package in which the kit is provided, or from any other similar time, such as the time of first use of the calibration chip 90. The ordinarily skilled artisan will find numerous variations can be effected without departure from the spirit and scope of this invention.

The patient uses the system by removing the testing instrument from the packaging and placing it on a firm surface. The next step is to remove a test strip and insert it in the testing instrument. Inserting the test strip activates the unit, eliminating the need for a power on/off button or switch. The patient then uses either a sampler from the kit or one procured separately to draw a sample of capillary blood. The sample is applied to the test strip, initiating a timing sequence, and the testing instrument displays the results after an appropriate time. Alternatively, the patient may first apply the blood sample to the test strip, then insert the strip into the testing instrument to activate the test cycle and read out of test results.

The subject invention provides improvements over existing technology in use today in several ways. The preferred embodiment of the invention eliminates the need for a patient to purchase a costly system to conduct routine testing of body fluids. It also eliminates the existing dependence on the customer to maintain the testing instrument and monitor or compensate for reagent lot differences. The invention provides this easy to use format for analytes such as glucose by incorporating advanced lens based optics and low cost modem electronics. The use of lens based optics permits the system to focus on small reaction area which reduces the size of the test pad. The resulting small test pad reduces the cost of the matrix employed and the quantity of expensive reagents needed to conduct an accurate assay using an oxidase and peroxidase chemistry. With a smaller test pad, a smaller sample volume is adequate. The system conserves the energy used and minimizes the amount of light required by the system to determine the color change. The optics modules are calibrated during the manufacture of the testing instrument.

An important feature in accordance with the invention is the manufacture and calibration of the testing instrument 151 for use with a specific quantity of test strips 1 which have been matched at the factory. This limits the need for calibration codes, and minimizes the maintenance required by the patient in the form of cleaning, battery replacement and calibration code changes. It also improves the system's ability to provide long term accurate results because a testing instrument is synchronized with only certain test strips. Once they have been used, a complete new kit is acquired with a testing instrument calibrated specifically for those test strips. This eliminates much of the compromise in system performance found in current products which have to work with strips made over a wide range of production conditions and input states.

The above are exemplary modes of carrying out the invention and are not intended to be limiting. It will be apparent to those skilled in the art that modifications thereto can be made without departure from the spirit and scope of the invention as set forth by the following claims.

What is claimed is:

1. A multi-use assay system for use with a removable test strip having a test pad, the multi-use assay system comprising:

an electronics printed circuit board having an alignment fixturing;

an optics system for alignment with the removable test strip, the optics system comprising a lens, an emitter and a detector, wherein the emitter and detector are mounted in the electronics printed circuit board relative to the alignment fixturing;

a housing for containing the optics system and holding the removable test strip in position relative to the optics system;

an optics block holder mounted in the electronics printed circuit board in alignment with the alignment fixturing, the optics block holder aligning the test strip to the test pad and positioning the optics system to focus light from the light emitter and to the detector; and a processor in communication with the light detector, the processor controlling the assay system such that a predetermined number of test strips are assayed based on signals from the light detector, wherein the predetermined number corresponds to the number of test strips of a set of one or more test strips.

2. The system of claim 1, further comprising a removable calibration chip, the predetermined number being provided by the removable calibration chip.

3. The system of claim 1; wherein the predetermined number is at least two.

4. The system of claim 2, wherein the predetermined number is at least two.

* * * * *